Aug. 25, 1936. W. I. JOHNSTON Plant Pat. 190
ROSE
Filed March 23, 1936
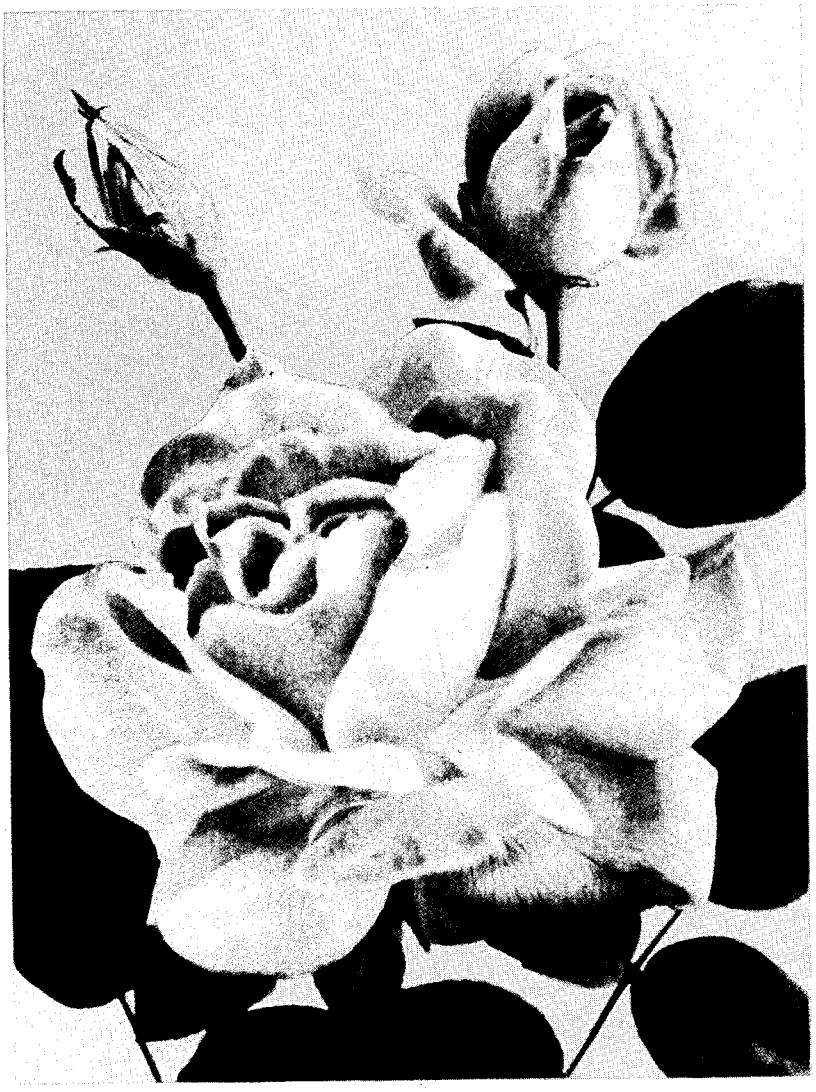
Inventor
W. I. Johnston
By Robb & Robb
Attorneys Patented Aug. 25, 1936

Plant Pat. 190

UNITED STATES PATENT OFFICE

190

ROSE

Walter Irwin Johnston, Portadown, Ireland, assignor to Jackson & Perkins Company, Newark, N. Y.

Application March 23, 1936, Serial No. 70,501

1 Claim. (Cl. 47—61)

The present invention relates to a new and distinct variety of Rose plant, a new development of the strain, originated many years ago by Samuel McGredy (1828–1903). This development is the result of extensive hybridizing of different seedlings of the McGredy strain carried on over a period of many years, including substantially the period of my life, during which I have been engaged in the art of breeding plants.

Since in the course of experimentation with respect to the cross hybridizing mentioned above, it was customary to inject ever so often some new, strong blood, such as species (wild types), Hybrid Perpetuals, etc., it is not practicable to set forth the complete pedigree where the plant is the culmination of many years of research and experimentation, as is the situation in the present instance. It is, therefore, sufficient to state that the seedling rose herein described came from crosses of numerous unnamed seedlings of the McGredy strain.

This new rose is a marked development because of the fact that it possesses all the good points and coloring of the *Pernetiana* strain with an elimination of all its weaknesses (poor vegetation, inclination to diseases, unstability of color), elimination of which was the objective of the experimentation carried through.

The plant has the true appearance and health of a pure Hybrid Tea with dominating characters all its own, which in fact denotes the great complexity of its ancestry. Those characters which mark it as a new type of garden rose are its very large size bloom of the unprecedented color of deep peach and the perfect health and vigor of the plant, developing unusually large foliage producing a large rounded plant not unlike a *Thuja globosa*. These characteristics have been found to be fixed by a sexual reproduction.

The following is a detailed description of the new rose, color designations according with the Gravereaux color chart:—

Parentage:

Seedling from unnamed seedlings of the McGredy strain.

Classification:

*Botanic.*—Hybrid tea.

*Commercial.*—Hybrid tea.

*Flower*

Blooming habit:

*Location where observations were made.*—Test gardens and fields of Jackson & Perkins Company, Newark, New York.

*Recurrent.*—Continuous.

Bud:

*Size.*—Very large.

*Form.*—Ovoid. Unaffected by wet or hot weather.

*Color.*—When sepals first divide—cerise suffused with orange. When petals begin to unfurl—peach strongly marked with yellow at base. When half blown:

*Inside of petals.*—Peach marked with orange.

*Reverse of petals.*—Same with yellow at base.

*Sepals.*—Branches, "hood" above bud. Curl back when bud half open.

*Calyx.*—Shape—funnel. Size—broad. Aspect—smooth. Odor when rubbed—none.

*Peduncle.*—Length—very long. Aspect—smooth. Color—medium green, bronzy on the sunny side. Strength—bending, heavy.

*Opening.*—Bud opens well; unaffected by adverse conditions.

Bloom:

*Size.*—Very large, average size when fully expanded 4" to 4½".

*Borne.*—Singly.

*Stems.*—Long, normal strength.

*Form.*—When first open, high center. Permanence, outer petals curl back.

*Petalage.*—Double (full but open center). Number of petals under normal conditions 25 to 30.

*Color.*—Center of flower—deep peach. Outer petals—deeper. Base of petals (aiglet)—yellow gradually blending into the petals. Inside of petals—deep peach. Reverse of petals—deep peach. General tonality from a distance—peach tending toward cerise.

*Variegations.*—None.

*Discoloration.*—Peach suffused with orange. Second day—same. Third day—paling toward cerise pink.

Petals:

*Texture.*—Thick; unaffected by wet or hot weather.

*Appearance.*—Inside—velvety. Outside—shiny.

*Form.*—Round.

*Arrangement.*—Imbricated (regularly arranged shinglelike). Petaloids in center, few.

*Persistence.*—Drop off cleanly.

*Fragrance.*—Moderate. Nature—Tea (average Hybrid Tea scent).

*Lasting quality.*—On the plant, very long. As cut flower—long.

Genital organs:

*Stamens, Anthers.*—Large, many. Color—yellow. Arrangement—regular round styles.

*Stamens, filaments (threads).*—Long. Color—white.

*Pollen.*—Lemon yellow.

*Styles.*—Bunched; even length, long; heavy.

*Stigmas.*—Color—white.

*Ovaries*—All enclosed in calyx.

Fruit:

Variety is fertile with its own pollen.

*Form.*—Flat headed, pear shaped.

*Aspect.*—Smooth.

*Color at maturity.*—Orange, scarlet.

*Sepals.*—Caducous (soon falling).

*Plant*

Form:

Bush.

Growth:

Very vigorous, branching.

Foliage:

Generally five leaflets.

*Size.*—Very large.

*Quantity.*—Abundant.

*Color—New foliage.*—Upper side—bronzy. Under side—Purplish bronze. *Old foliage.*—Upper side—dark green. Under side—lighter green.

*Shape.*—Oval pointed.

*Texture.*—Upper side—leathery. Under side—smooth. Ribs and veins—ordinary.

*Edge.*—Serrated (saw toothed).

*Serration.*—Single, small.

*Rachis.*—Color reddish; under side prickles.

*Stipules.*—Medium smooth.

*Disease resistance.*—Resistant.

Wood:

*New wood.*—Color—reddish. Bark—smooth.

*Old wood.*—Color—green. Bark—smooth.

Thorns: (Divided into thorns, prickles, and short needles).

*Thorns.*—Quantity—on main stalks from base, few on laterals from stalk, few. Form—broad base, medium, hooked downward. Color when young—red. Position—irregular.

*Prickles.*—Quantity—on main stalks, none; on laterals, none.

I claim:

A new and distinct variety of rose plant constituting a new type of garden rose, characterized by its production of a vigorous well rounded plant of unusually large foliage and by its very large size peach-colored blossom, substantially as shown and described.

WALTER IRWIN JOHNSTON.